United States Patent
Pieloch

(10) Patent No.: US 7,025,965 B1
(45) Date of Patent: Apr. 11, 2006

(54) METHOD OF USE AND DOSAGE COMPOSITION OF BLUEGREEN ALGAE EXTRACT FOR INFLAMMATION IN ANIMALS

(75) Inventor: Mark J. Pieloch, Syracuse, NE (US)

(73) Assignee: Pharma Chemie, Inc., Syracuse, NE (US)

( * ) Notice: Subject to any disclaimer, the term of this patent is extended or adjusted under 35 U.S.C. 154(b) by 0 days.

(21) Appl. No.: 10/365,047

(22) Filed: Feb. 12, 2003

(51) Int. Cl.
- *A61K 35/80* (2006.01)
- *A61K 9/00* (2006.01)
- *A61K 47/00* (2006.01)
- *A23K 1/165* (2006.01)

(52) U.S. Cl. .................. 424/195.17; 424/400; 424/439; 424/442

(58) Field of Classification Search ............ 424/195.17, 424/400, 439, 442
See application file for complete search history.

(56) References Cited

U.S. PATENT DOCUMENTS 6,350,485 B1 * 2/2002 Brunner

FOREIGN PATENT DOCUMENTS

JP 358065216 A * 4/1983

OTHER PUBLICATIONS

Romay et al., Antioxidant and anti-inflammatory properties of C-phycocyanin from blue algae, Inflammation Research, vol. 47 (1998), pp. 36-41.*

* cited by examiner

*Primary Examiner*—Susan Coe
*Assistant Examiner*—Randall Winston
(74) *Attorney, Agent, or Firm*—McKee, Voorhees & Sease, P.L.C.

(57) ABSTRACT

A means and method for treating inflammation and pain in animals is described. The compounds include phycocyanin in a pharmaceutically acceptable carrier. Phycocyanin has been found to be a COX-2 selective agent, and therefore alleviates pain and inflammation without the side effects that occur with NSAIDs that are not COX-2 selective.

12 Claims, No Drawings

US 7,025,965 B1

METHOD OF USE AND DOSAGE COMPOSITION OF BLUEGREEN ALGAE EXTRACT FOR INFLAMMATION IN ANIMALS

FIELD OF THE INVENTION

This invention relates to compositions and methods for treating inflammation in animals. Specifically, this invention relates to COX-2 selective inhibitors, methods of their use and manufacture.

BACKGROUND OF THE INVENTION

Arthritis is a complaint suffered by all types of animals that have an endoskeletal supporting structure composed of bone, ligaments, and cartilage. Such animals include humans, cats, dogs, horses, and many others.

There are two major forms of arthritis. Rheumatoid arthritis is a common form of arthritis which involves inflammation of the joints, swelling, pain, and loss of function. The primary symptom of rheumatoid arthritis is inflammation of the synovial membrane. The membrane thickens and synovial fluid accumulates. The resulting pressure causes pain and tenderness.

The most common form of arthritis, osteoarthritis, is a degenerative joint disease that is far more common than rheumatoid arthritis. It is characterized by the deterioration of articular cartilage and the formation of new bone in the subchondral areas and at the margins of the joint. The cartilage slowly degenerates and as the bone ends become exposed small bumps of new osseous tissue are deposited on them. These bumps decrease the space in the bone cavity and restrict joint movement.

Both forms of arthritis are more common in older animals, although they are still found in young animals, usually due to a genetic disorder.

Arthritis in animals may also be caused by Lyme disease and primary cartilage degeneration in young dogs.

Arthritis is a slowly progressive disease that starts with almost undetectable discomfort, and may progress to the point where the animal refuses to stand, walk, or even eat. In companion pets, the pet owner may first notice the disease when the animal has slight difficulty in getting up and down, climbing stairs, jumping up on furniture or into cars, soreness hours after exercise, or grumpiness.

Non-steroidal anti-inflammatory agents (NSAIDs) such as aspirin, ibuprofen, ketoprofen and naproxen, are effective in reducing arthritic pain. NSAIDs relieve pain by acting on the cyclooxygenase portion of the enzyme prostaglandin synthase. Two isoforms of cyclooxygenase exist, cyclooxygenase-1 (COX-1) and cyclooxygenase-2 (COX-2). Both isoforms catalyze the reaction that converts arachidonic acid into a class of hormones known as eicosinoids, which include prostaglandins, prostacyclins, and thromboxanes. COX-1 is expressed in all mammalian tissues, and serves a variety of homeostatic physiologic functions. It is responsible for the production of protective prostaglandins in the kidney and the stomach, as well as the functional thromboxane of platelets. In contrast, COX-2 is not normally found in most tissues, and is expressed under conditions of tissue damage. COX-2 leads to the biosynthesis of prostaglandins, triggering pain and inflammatory responses.

The inhibition of COX-2 is critical to the anti-inflammatory effects of NSAIDs, while the vast majority of side effects can be linked to the inhibition of COX-1. Typical side effects of NSAIDs include abdominal pain, diarrhea, vomiting, stomach and intestinal ulcers, kidney and liver damage, and decreased blood clotting. Drugs that selectively target the COX-2 enzyme can be expected to maintain clinical efficacy with a reduction in side effects.

Coxib drugs are compounds which target the inhibition of the inducible enzyme COX-2 while sparing the activity of COX-1. Currently available Coxib drugs in human medicine include Vioxx® (rofecoxib) and Celebrex® (celecoxib). Duramaxx® (deracoxib) is currently the only Coxib drug approved for veterinary use.

There is therefore a continuing need in the art for the development of medications that are COX-2 selective for treating inflammation and pain in animals.

Accordingly, it is a primary objective of the present invention to provide a composition and method for treating arthritis and other inflammatory disorders in animals, especially companion animals, using a COX-2 selective inhibitor.

It is a further objective of the present invention to provide a composition and method for treating inflammatory disorders in animals that is derived from blue-green algae.

It is still a further objective of the present invention to provide a composition and method for treating inflammatory disorders in animals that is less toxic and has fewer side effects than COX-1 inhibitors.

It is yet a further objective of the present invention to provide a composition and method for treating inflammatory disorders in animals that is palatable and easy to administer.

It is a further objective of the present invention to provide a composition and method for treating inflammatory disorders in animals that is orally active.

The method and means of accomplishing each of the above objectives as well as others will become apparent from the detailed description of the invention which follows hereafter.

SUMMARY OF THE INVENTION

The invention describes a method and composition for treating arthritis and other inflammatory disorders in animals using a composition containing phycocyanin as an effective component thereof. In particular, the invention is directed to treating pain and inflammation in companion animals, and especially dogs, cats, and horses.

According to the invention, blue-green algae extract and, more particularly, phycocyanin has been found to function as a COX-2 inhibitor that is effective in treating arthritis and other inflammatory conditions in animals. The extract is administered in a form that is pharmaceutically acceptable and palatable for animals. The invention embraces prodrugs, racemic mixtures, as well as enantiomeric forms of the compound.

DETAILED DESCRIPTION OF THE PREFERRED EMBODIMENT

The present invention relates to the development of pharmaceutical compositions and methods for treating pain and inflammation and animals using extract from blue-green algae and, more specifically, phycocyanin.

Blue-green algae (also known as cyanobacteria), so called because of their content of chlorophyll and the blue pigment phycocyanin, are among the most primitive living organisms on Earth. Although they are technically classified as bacteria, they share properties with bacteria and with plants.

Phycocyanin is one of the main natural pigments commercially produced from algae. In the living algae cell, phycocyanin serves as a protein storage unit and as an antioxidant, protecting the cell from certain light wavelengths. Phycocyanin is a nontoxic and non-carcinogenic pigment that has gained importance in coloring products such as fermented milk products, ice cream, chewing gum, soft drinks, alcoholic drinks, desserts, cake decorations, milk shakes, and cosmetics. It has now been found that phycocyanin is effective in reducing inflammation in animals through its ability to selectively inhibit the COX-2 enzyme.

While blue-green algae is considered one of the primary sources of phycocyanin, the present invention is intended to encompass phycocyanin derived from any source, including red algae, as well as artificially synthesized phycocyanin.

The term "animal" as used herein includes without limitation domesticated animals such as cattle, horses, swine, sheep, dogs, cats, goats and the like. The tests hereinafter shown in the examples are particularly illustrative for dogs and horses, but indicate usage for other domesticated animals including cats and other mammals. It is believed treatment may also be useful for birds or fish. Needless to say, the natural enjoyment of pets would be significantly increased if their general well being and health is maintained. This includes the ability of the animal to function normally without the deleterious affects of arthritis and other inflammatory diseases and disorders.

As used herein, the term "pharmaceutically acceptable" means a composition for use in the pharmaceutical or veterinary art that is nontoxic or otherwise not pharmaceutically or veterinary unacceptable. Administration of the therapeutically active compound phycocyanin to achieve physiological results of the present invention can be via any of the accepted modes of administration for systemically active substances to animals. These methods include oral, parenteral, and otherwise systemic, aerosol, and topical forms, as well as sustained release systems, etc.

The compositions of the present invention may be any of those known in the pharmaceutical and veterinary arts which are suitable for the method of administration and dosage required in any particular circumstance. In the case of both pharmaceutical and veterinary applications, such compositions may include tablets, pills, capsules, powders, aerosols, suppositories, skin patches, parenterals, and oral liquids including oil aqueous suspensions, solutions and emulsions. It may also include long-acting injectables and sustained-release devices.

Unit dosage forms such as tablets and capsules may contain any suitable predetermined amount of phycocyanin, and may be administered one or more at a time at regular intervals as later described. Such unit dosage forms, however, should with a broad range guideline contain a concentration of 0.1% to 20% by weight of one or more forms of the active phycocyanin.

As used herein the term "effective amount" refers to a concentration of phycocyanin that is effective in treating inflammation or a particular inflammatory disorder, such as arthritis, in terms of reducing inflammation and/or pain in the animal to a degree greater than would have been achieved without treatment with phycocyanin.

The compositions of the present invention may be generally used for the treatment of arthritis and other acute and chronic inflammatory disorders including, but not limited to, hip dysplasia, osteochondritis, spondylitis, spondylosis, and postoperative pain. As already noted above, the phycocyanin can be administered in any effectively pharmaceutically acceptable form, e.g. in topical, lavage, oral, suppository, parenteral, or infusible dosage forms, as a topical, buccal, sublingual, or nasal spray or in any other manner effective to deliver the agents. The route of administration will preferably be designed to optimize delivery and/or localization of the agents to target cells.

In addition to the active compounds i.e. phycocyanin, the pharmaceutical compositions of this invention may contain suitable excipients and auxiliaries which facilitate processing of the active compounds into preparations which can be used pharmaceutically. Oral dosage forms encompass tablets, capsules, powders, and granules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, dissolving, and lyophilizing processes. The processes to be used will depend ultimately on the physical properties of the active ingredient used.

Suitable excipients are, in particular, fillers such as sugars for example, lactose or sucrose, mannitol or sorbitol, cellulose preparations and/or calcium phosphates, for example, tricalcium phosphate, microcrystalline cellulose, or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as croscarmellose sodium, carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices. For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added.

Other pharmaceutical preparations which can be used orally include capsules made of gelatin or vegetable origin. The capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffinhydrocarbons, polyethylene glycols, or higher alkanols. In addition, it is also possible to use gelatin or vegetable origin rectal capsules which consist of a combination of the active compounds with a base. Possible base materials include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

In addition to administration with conventional carriers, active ingredients may be administered by a variety of specialized delivery drug techniques which are known to those of skill in the art, such as portable infusion pumps.

The phycocyanin compositions of the present invention are administered along with a pharmaceutically/veterinary acceptable carrier in an amount sufficient to treat an inflammatory disorder. The dosing range of the phycocyanin compositions will vary depending on a number of factors, such as route of administration, dosing schedule, type of inflammatory disorder, severity of the inflammatory disorder, etc. In general, the therapeutic dose of phycocyanin may range between about 0.1–1000 mg/kg/day, with about 0.5 mg/lb/day (~0.23 mg/kg/day) to 15 mg/lb/day (~6.80 mg/kg/day) being preferred, and about 0.7 mg/lb/day (~0.32 mg/kg/day) to 11.2 mg/lb/day (~5.08 mg/kg/day) being most preferred. The foregoing doses may be administered as a single dose or may be divided into multiple doses for administration. For the sake of convenience, once a day dosing is preferred. Of course, it would be known to those in the art that sustained release systems can be used to provide less frequent administration to achieve the required dosage level.

Other drugs besides phycocyanin which are compatible with the carrier ingredients may also be incorporated into the carrier. Such drugs may be readily ascertained by those of ordinary skill in the art and may include, for instance, antibiotics, other antiinflammatory agents, analgesics, nutraceuticals, corticosteroids, vitamins, etc.

It is understood that the present invention contemplates the use of not only phycocyanin, but its prodrugs which metabolize to the compound and the analogues and biologically active salt forms thereof, as well as optical isomers which provide the same pharmaceutical results.

The following examples are offered to illustrate but not limit the invention. Thus, they are presented with the understanding that various formulation modifications as well as method of delivery modifications may be made and still be within the spirit of the invention.

EXAMPLE 1

Use of Phycocyanin for Treating Osteoarthritis and other Joint Disorders in Dogs A study is currently being conducted to determine the efficacy of phycocyanin in five different weight categories and five different dosage categories on a mg/lb basis as an anti-inflammatory in dogs with osteoarthritis or other joint disorders.

The phycocyanin composition being tested contains Aphanin™, a phycocyanin supplement that contains approximately 25% by weight phycocyanin. The composition is a liver and roast beef, palatable, chewable dog tablet that contains the following amounts of Aphanin™ per dosage unit: 31.25 mg, 62.5 mg, 125 mg, 250 mg, and 500 mg.

Five study groups were defined by weight. Various dosage amounts were included in each weight category. There were a total number of 71 randomly chosen dogs in the study. Weight range categories were (in pounds): 5–15, 16–30, 31–60, 61–120, and 120+pounds. Table 1 sets forth the study groups:

TABLE 1

Daily Aphanin Dosing in mg
(Number of Dogs Per Dosing Regimen)

| Dog Weight in Pounds | A | B | C | D | E |
|---|---|---|---|---|---|
| 5–15 | 7.8125 mg (0) | 15.625 mg (0) | 31.25 mg (1) | 62.5 mg (2) | 125 mg (1) |
| 16–30 | 15.625 mg (0) | 31.25 mg (0) | 62.5 mg (2) | 125 mg (4) | 250 mg (2) |
| 31–60 | 31.25 mg (2) | 62.5 mg (2) | 125 mg (2) | 250 mg (3) | 500 mg (1) |
| 61–120 | 62.5 mg (13) | 125 mg (12) | 250 mg (7) | 500 mg (7) | 1000 mg (8) |
| 120+ | 125 mg (1) | 250 mg (0) | 500 mg (1) | 1000 mg (0) | 2000 mg (0) |

In the study, groups A–E were dosed as follows:
A: 0.7 mg/lb
B: 1.4 mg/lb
C: 2.8 mg/lb
D: 5.6 mg/lb
E: 11.2 mg/lb The dogs are being evaluated based on the following factors:
  degree of mobility change;
  whether the dog seems happier and/or more alert;
  whether the dog can get up from a lying position easier;
  whether the pain level has diminished for the dog;
  whether the dog goes outside more readily;
  whether the dog plays with toys or children more readily;
  whether there an increase in activity level while outside;
  whether the dog was sick at any time during the study;
  whether there was any reason to discontinue the study; and
  whether there was any medication change in the study.

Preliminary Results

Aphanin Canine Study Summary

| Dosage Group | Dogs per Group | Month 1 Results Averaged |
|---|---|---|
| 0.7 mg/lb/day | 16 | 2.96 |
| 1.4 mg/lb/day | 14 | 2.71 |
| 2.8 mg/lb/day | 13 | 2.53 |
| 5.6 mg/lb/day | 16 | 2.72 |
| 11.2 mg/lb/day | 12 | 2.61 |
| Total | 71 | Average: 2.73 |

Interim Study Observations: Month 1 of 4

After one month of dosing Aphanin at five (5) different dosage ranges on a mg/lb/day basis, it appears that Aphanin is effective in treating pain and discomfort in arthritic dogs. The dose response curve appears flat; which means that as the dose of Aphanin increases on a mg/lb/day basis, the clinical response to the dog remains constant.

Date: Month 1 of 4
Canine
Study Group A
(0.7 mg/lb/day)

| Number | Mobility | Alert | Change Position | Pain Level | Outside Readily | Plays More | Increase Activity | Sick | Stop Use | Rx Change | Dosage | Total | Average |
|---|---|---|---|---|---|---|---|---|---|---|---|---|---|
| A-31/60-01 | 3 | 3 | 3 | 3 | 4 | 3 | 4 | n | n | n | 31.25 mg | 23 | 3.29 |
| A-31/60-02 | 3 | 4 | 3 | 4 | 1 | 4 | 4 | n | n | n | 31.25 mg | 23 | 3.29 |
| A-61/120-01 | 1 | 1 | 1 | 1 | 2 | 1 | 2 | n | n | n | 62.5 mg | 9 | 1.29 |
| A-61/120-02 | 4 | 5 | 5 | 5 | 1 | 5 | 5 | n | n | n | 62.5 mg | 30 | 4.29 |
| A-61/120-03 | 3 | 3 | 2 | 2 | 2 | 2 | 3 | n | n | n | 62.5 mg | 17 | 2.43 |
| A-61/120-04 | 5 | 5 | 5 | 5 | 5 | 5 | 5 | n | n | n | 62.5 mg | 35 | 5.00 |
| A-61/120-05 | 2 | 3 | 1 | 2 | 2 | 3 | 3 | n | n | n | 62.5 mg | 16 | 2.29 |
| A-61/120-06 | 2 | 1 | 3 | 3 | 1 | 1 | 1 | n | n | n | 62.5 mg | 12 | 1.71 |
| A-61/120-07 | 3 | 4 | 3 | 4 | 5 | 5 | 5 | n | n | n | 62.5 mg | 29 | 4.14 |
| A-61/120-08 | 1 | 1 | 2 | 1 | 1 | 1 | 1 | n | n | n | 62.5 mg | 8 | 1.14 |
| A-61/120-09 | 4 | 4 | 5 | 4 | 1 | 4 | 4 | n | n | n | 62.5 mg | 26 | 3.71 |
| A-61/120-10 | 4 | 4 | 2 | 3 | 4 | 5 | 5 | n | n | n | 62.5 mg | 27 | 3.86 |
| A-61/120-11 | 1 | 1 | 1 | 1 | 1 | 1 | 1 | n | n | n | 62.5 mg | 7 | 1.00 |
| A-61/120-12 | 2 | 2 | 2 | 2 | 3 | 3 | 3 | n | n | n | 62.5 mg | 17 | 2.43 |
| A-61/120-13 | 4 | 5 | 4 | 3 | 4 | 4 | 5 | n | n | n | 62.5 mg | 29 | 4.14 |
| A-121+-01 | 4 | 4 | 4 | 5 | 2 | 1 | 4 | y | y | n | 125 mg | 24 | 3.43 |
| Category Average | 2.88 | 3.13 | 2.88 | 3.00 | 2.44 | 3.00 | 3.44 | | | | | | 2.96 |
| Average of all categories | | | 2.96 | | | | | | | | | | |

Legend: Dog Number
A-31/60-01
A = Dosing Group (0.7 mg/lbs/day)
31/60 = Dog Weight Range in lbs
01 = Dog Study Number Date: Month 1 of 4
Canine
Study Group B
(1.4 mg/lb/day)

| Number | Mobility | Alert | Change Position | Pain Level | Outside Readily | Plays More | Increase Activity | Sick | Stop Use | Rx Change | Dosage | Total | Average |
|---|---|---|---|---|---|---|---|---|---|---|---|---|---|
| B-31/60-01 | 1 | 1 | 1 | 2 | 3 | 3 | 3 | n | n | n | 62.5 mg | 14 | 2.00 |
| B-31/60-02 | 2 | 4 | 2 | 3 | 1 | 2 | 3 | n | n | n | 62.5 mg | 17 | 2.43 |
| B-61/120-01 | 3 | 3 | 1 | 2 | 1 | 3 | 3 | n | n | n | 125 mg | 16 | 2.29 |
| B-61/120-02 | 3 | 4 | 3 | 3 | 4 | 5 | 3 | n | n | n | 125 mg | 25 | 3.57 |
| B-61/120-03 | 2 | 3 | 1 | 2 | 3 | 3 | 3 | n | n | n | 125 mg | 17 | 2.43 |
| B-61/120-04 | 5 | 5 | 5 | 4 | 5 | 4 | 5 | n | n | n | 125 mg | 33 | 4.71 |
| B-61/120-05 | 3 | 3 | 3 | 3 | 3 | 1 | 3 | n | n | n | 125 mg | 19 | 2.71 |
| B-61/120-06 | 3.5 | 4.5 | 3.5 | 4 | 4.5 | 1 | 5 | y | n | n | 125 mg | 26 | 3.71 |
| B-61/120-07 | 4 | 4 | 4 | 4 | 4 | 1 | 4 | n | n | n | 125 mg | 25 | 3.57 |
| B-61/120-08 | 1 | 1 | 1 | 1 | 1 | 1 | 1 | n | n | n | 125 mg | 7 | 1.00 |
| B-61/120-09 | 1 | 2 | 1 | 1 | 1 | 1 | 3 | n | n | y | 125 mg | 10 | 1.43 |
| B-61/120-10 | 3 | 3 | 3 | 4 | 4 | 4 | 4 | n | n | n | 125 mg | 25 | 3.57 |
| B-61/120-11 | 1 | 1 | 1 | 1 | 1 | 1 | 1 | n | n | n | 125 mg | 7 | 1.00 |
| B-61/120-12 | 4 | 1 | 3 | 3 | 4 | 5 | 5 | n | n | n | 125 mg | 25 | 3.57 |
| | | | | | | | | | | | | | 2.71 |
| Category Average | 2.61 | 2.82 | 2.32 | 2.64 | 2.82 | 2.50 | 3.29 | | | | | | |
| Average of all categories | | | 2.71 | | | | | | | | | | |

Legend: Dog Number
B-31/60-01
B = Dosing Group (1.4 mg/lb/day)
31/60 = Dog Weight Range in lbs
01 = Dog Study Number Date: Month 1 of 4
Canine
Study Group C
(2.8 mg/lb/day)

| Number | Mobility | Alert | Change Position | Pain Level | Outside Readily | Plays More | Increase Activity | Sick | Stop Use | Rx Change | Dosage | Total | Average |
|---|---|---|---|---|---|---|---|---|---|---|---|---|---|
| C-05/15-01 | 3 | 3 | 1 | 3 | 3 | 3 | 3 | n | n | n | 31.25 mg | 19 | 2.71 |
| C-16/30-06 | 4 | 4 | 3 | 3 | 3 | 4 | 3 | n | n | n | 62.5 mg | 24 | 3.43 |
| C-16/30-07 | 3 | 4 | 3 | 3 | 2 | 3 | 2 | n | n | n | 62.5 mg | 20 | 2.86 |
| C-31/60-15 | 2 | 2 | 2 | 2 | 1 | 1 | 2 | n | n | n | 125 mg | 12 | 1.71 |
| C-31/60-16 | 2 | 4 | 1 | 2 | 5 | 1 | 5 | n | n | n | 125 mg | 20 | 2.86 |
| C-61/120-22 | 2 | 2 | 3 | 3 | 2 | 3 | 3 | n | n | n | 250 mg | 18 | 2.57 |
| C-61/120-23 | 2 | 2 | 1 | 1 | 2 | 1 | 2 | n | n | n | 250 mg | 11 | 1.57 |
| C-61/120-24 | 1 | 3 | 1 | 1 | 1 | 3 | 1 | y | n | n | 250 mg | 11 | 1.57 |
| C-61/120-25 | 2 | 4 | 3 | 3 | 5 | 4 | 3 | y | y | n | 250 mg | 24 | 3.43 |
| C-61/120-26 | 4 | 4 | 4 | 4 | 1 | 4 | 4 | n | n | n | 250 mg | 25 | 3.57 |
| C-61/120-27 | 2 | 3 | 2 | 1 | 1 | 3 | 2 | n | n | n | 250 mg | 14 | 2.00 |
| C-61/120-28 | 3 | 2 | 2 | 2 | 3 | 2 | 1 | n | n | n | 250 mg | 15 | 2.14 |
| C-121+-47 | 3 | 2 | 2 | 1 | 1 | 4 | 4 | n | n | n | 500 mg | 17 | 2.43 |
| Category Average | 2.54 | 3.00 | 2.15 | 2.23 | 2.31 | 2.77 | 2.69 | | | | | | 2.53 |
| Average of all categories | | | 2.53 | | | | | | | | | | |

Legend: Dog Number
C-31/60-01
C = Dosing Group (2.8 mg/lb/day)
31/60 = Dog Weight Range in lbs
01 = Dog Study Number Date: Month 1 of 4
Canine
Study Group D
(5.6 mg/lb/day)

| Number | Mobility | Alert | Change Position | Pain Level | Outside Readily | Plays More | Increase Activity | Sick | Stop Use | Rx Change | Dosage | Total | Average |
|---|---|---|---|---|---|---|---|---|---|---|---|---|---|
| D-5/15-02 | 2 | 4 | 3 | 3 | 1 | 1 | 1 | n | n | n | 62.5 mg | 15 | 2.14 |
| D-5/15-03 | 3 | 3 | 3 | 3 | 4 | 4 | 3 | | | | 62.5 mg | 23 | 3.29 |
| D-16/30-08 | 5 | 5 | 5 | 5 | 5 | 5 | 5 | n | n | n | 125 mg | 35 | 5.00 |
| D-16/30-09 | 2 | 3 | 3 | 2 | 3 | 3 | 2 | n | n | n | 125 mg | 18 | 2.57 |
| D-16/30-10 | 1 | 1 | 2 | 2 | 1 | 1 | 1 | n | n | n | 125 mg | 9 | 1.29 |
| D-16/30-11 | 3 | 3 | 4 | 3 | 4 | 3 | 4 | n | n | n | 125 mg | 24 | 3.43 |
| D-31/60-17 | 3 | 2 | 4 | 3 | 2 | 2 | 2 | n | n | n | 250 mg | 18 | 2.57 |
| D-31/60-18 | 3 | 4 | 4 | 4 | 3 | 3 | 3 | n | n | n | 250 mg | 24 | 3.43 |
| D-31/60-45 | 3 | 5 | 3 | 4 | 5 | 4 | 3 | y | n | n | 250 mg | 27 | 3.86 |
| D-61/120-30 | 1 | 3 | 1 | 1 | 2 | 2 | 2 | n | n | n | 500 mg | 12 | 1.71 |
| D-61/120-31 | 1 | 1 | 1 | 1 | 1 | 1 | 1 | n | n | n | 500 mg | 7 | 1.00 |
| D-61/120-32 | 2 | 3 | 2 | 3 | 1 | 2 | 3 | n | n | n | 500 mg | 16 | 2.29 |
| D-61/120-33 | 5 | 3 | 5 | 4 | 1 | 4 | 4 | y | y | n | 500 mg | 26 | 3.71 |
| D-61/120-34 | 2 | 2 | 3 | 2 | 1 | 1 | 2 | n | n | n | 500 mg | 13 | 1.86 |
| D-61/120-35 | 2 | 2 | 3 | 2 | 1 | 1 | 2 | n | n | n | 500 mg | 13 | 1.86 |
| D-61/120-36 | 3 | 2 | 4 | 1 | 5 | 5 | 5 | n | n | n | 500 mg | 25 | 3.57 |
| Category Average | 2.56 | 2.88 | 3.13 | 2.69 | 2.50 | 2.63 | 2.69 | | | | | | 2.72 |
| Average of all categories | | | 2.72 | | | | | | | | | | |

Legend: Dog Number
D-31/60-02
D = Dosing Group (5.6 mg/lb/day)
31/60 = Dog Weight Range in lbs
01 = Dog Study Number

| | | | | | Date: Month 1 of 4 Canine Study Group E (11.2 mg/lb/day) | | | | | | | | |
|---|---|---|---|---|---|---|---|---|---|---|---|---|---|
| Number | Mobility | Alert | Change Position | Pain Level | Outside Readily | Plays More | Increase Activity | Sick | Stop Use | Rx Change | Dosage | Total | Average |
| E-05/15-04 | 4 | 5 | 4 | 4 | 4 | 4 | 4 | n | n | n | 125 mg | 29 | 4.14 |
| E-16/30-12 | 3 | 3 | 4 | 3 | 3 | 2 | 4 | n | n | n | 250 mg | 22 | 3.14 |
| E-16/30-13 | 1 | 1 | 1 | 1 | 1 | 1 | 1 | n | n | n | 250 mg | 7 | 1.00 |
| E-31/60-46 | 3 | 3 | 3 | 3 | 3 | 2 | 4 | n | n | n | 500 mg | 21 | 3.00 |
| E-61/120-37 | 4 | 4 | 3 | 3 | 4 | 4 | 4 | n | n | n | 1000 mg | 26 | 3.71 |
| E-61/120-38 | 4 | 4 | 4 | 5 | 1 | 1 | 4 | n | n | n | 1000 mg | 23 | 3.29 |
| E-61/120-39 | 4 | 5 | 4 | 4 | 5 | 5 | 4 | n | n | n | 1000 mg | 31 | 4.43 |
| E-61/120-40 | 3 | 4 | 3 | 2 | 4 | 3 | 4 | n | n | n | 1000 mg | 23 | 3.29 |
| E-61/120-41 | 2 | 2 | 1 | 1 | 1 | 2 | 2 | n | n | n | 1000 mg | 11 | 1.57 |
| E-61/120-42 | 1 | 1 | 1 | 1 | 1 | 1 | 1 | n | n | n | 1000 mg | 7 | 1.00 |
| E-61/120-43 | 1 | 2 | 1 | 1 | 1 | 2 | 2 | n | n | n | 1000 mg | 10 | 1.43 |
| E-61/120-49 | 1 | 2 | 1 | 1 | 1 | 1 | 2 | n | n | n | 1000 mg | 9 | 1.29 |
| Category Average | 2.58 | 3.00 | 2.50 | 2.42 | 2.42 | 2.33 | 3.00 | | | | | | 2.61 |
| Average of all categories | | | 2.61 | | | | | | | | | | |

Legend: Dog Number
E-31/60-04
E = Dosing Group (11.2 mg/lb/day)
31/60 = Dog Weight Range in lbs
01 = Dog Study Number The preliminary results of the study demonstrate that the use of phycocyanin improves motility and activity in the dogs tested.

EXAMPLE 2

Use of Phycocyanin for Treating Osteoarthritis and other Joint Disorders in Horses A study is being conducted to determine the efficacy of phycocyanin in five different weight categories and five different dosage categories on a mg/lb basis as an anti-inflammatory in horses with osteoarthritis or other joint disorders.

The phycocyanin composition being tested contains Aphanin™. The composition is a sweet apple and molasses flavored, palatable granule that contains the following amounts of Aphanin™ per dosage unit: 500 mg, 1000 mg, 2000 mg, 4000 mg, and 6000 mg.

Five study groups were defined by weight. Various dosage amounts were included in each weight category. The study group was comprised of 41 horses with an average weight of 1100 pounds.

The groups were dosed as follows:

| 9 horses: | 500 mg/day | (0.455 mg/lb) |
| 9 horses: | 1000 mg/day | (0.91 mg/lb) |
| 7 horses: | 2000 mg/day | (1.82 mg/lb) |
| 8 horses: | 4000 mg/day | (3.64 mg/lb) |
| 8 horses: | 6000 mg/day | (5.46 mg/lb) |

The horses are being evaluated based on the following factors:
  degree of mobility change;
  whether the horse seems happier and/or more alert;
  whether the horse can get up from a lying position easier;
  whether the pain level has diminished for the horse;
  whether there an increase in activity level while outside;
  whether the horse was sick at any time during the study;
  whether there was any reason to discontinue the study; and
  whether there was any medication change during the study.

Preliminary Results

| | Aphanin Equine Study Summary | |
|---|---|---|
| Dosage Group | Horses per Group | Month 1 Results Averaged |
| 0.45 mg/lb/day | 9 | 2.44 |
| 0.91 mg/lb/day | 9 | 2.16 |
| 1.82 mg/lb/day | 8 | 2.80 |
| 3.64 mg/lb/day | 7 | 1.80 |
| 5.46 mg/lb/day | 8 | 2.45 |
| Total | 71 | Average: 2.33 |

After one month of dosing Aphanin at five (5) different dosage ranges on a mg/lb/day basis, it appears that Aphanin is effective in treating pain and discomfort in arthritic horses. The dose response curve appears flat; which means that as the dose of Aphanin increases on a mg/lb/day basis, the clinical response to the horse remains constant.

Date: Month 1 of 4
Dosage: 500 mg/day
Duration: 4 months
Equine
Study Group A
(0.455 mg/lb/day)

| Number | Mobility | Alertness | Change Positions | Pain Level | Increase Activity | Sick | Non-Use | RX Changes | Total | Average |
|---|---|---|---|---|---|---|---|---|---|---|
| E-01-A | 3 | 4 | 4 | 3 | 3 | n | n | n | 17 | 3.40 |
| E-02-A | 2 | 1 | 2 | 2 | 2 | n | n | n | 9 | 1.80 |
| E-03-A | 4 | 4 | 3 | 4 | 4 | n | n | n | 19 | 3.80 |
| E-04-A | 2 | 3 | 3 | 3 | 3 | n | n | n | 14 | 2.80 |
| E-05-A | 2 | 4 | 4 | 2 | 3 | n | n | n | 15 | 3.00 |
| E-06-A | 2 | 2 | 1 | 2 | 2 | n | n | n | 9 | 1.80 |
| E-07-A | 3 | 3 | 3 | 4 | 4 | n | n | n | 17 | 3.40 |
| E-08-A | 1 | 1 | 1 | 1 | 1 | n | n | n | 5 | 1.00 |
| E-09-A | 1 | 1 | 1 | 1 | 1 | n | n | n | 5 | 1.00 |
| Category Average | 2.22 | 2.56 | 2.44 | 2.44 | 2.56 | | | | | 2.44 |
| Average of all categories | | | 2.44 | | | | | | | |

Legend: Horse Number
E-03-A
E = Equine
03 = Horse Study Number
A = Horse Study Group Date: Month 1 of 4
Dosage: 1000 grams/day
Duration: 4 months
Equine
Study Group B
(0.91 mg/lb/day)

| Number | Mobility | Alertness | Change Positions | Pain Level | Increase Activity | Sick | Non-Use | RX Changes | Total | Average |
|---|---|---|---|---|---|---|---|---|---|---|
| E-01-B | 3 | 3 | 1 | 3 | 3 | n | n | n | 13 | 2.60 |
| E-02-B | 2 | 2 | 2 | 2 | 2 | n | n | n | 10 | 2.00 |
| E-03-B | 3 | 1 | 3 | 3 | 4 | n | n | n | 14 | 2.80 |
| E-04-B | 3 | 2 | 4 | 2 | 1 | n | n | n | 12 | 2.40 |
| E-05-B | 1 | 4 | 3 | 2 | 3 | n | n | n | 13 | 2.60 |
| E-06-B | 1 | 1 | 1 | 1 | 1 | n | n | n | 5 | 1.00 |
| E-07-B | 3 | 2 | 2 | 1 | 1 | n | n | n | 9 | 1.80 |
| E-08-B | 4 | 3 | 3 | 3 | 2 | n | n | n | 15 | 3.00 |
| E-09-B | 1 | 2 | 1 | 1 | 1 | n | n | n | 6 | 1.20 |
| Category Average | 2.33 | 2.22 | 2.22 | 2.00 | 2.00 | | | | | 2.16 |
| Average of all categories | | | 2.16 | | | | | | | |

Legend: Horse Number
E-03-B
B = Equine
03 = Horse Study Number
B = Horse Study Group Date: Month 1 of 4
Dosage: 2000 grams/day
Duration: 4 months
Equine
Study Group C
(1.82 mg/lb/day)

| Number | Mobility | Alertness | Change Positions | Pain Level | Increase Activity | Sick | Non-Use | RX Changes | Total | Average |
|---|---|---|---|---|---|---|---|---|---|---|
| E-01-C | 4 | 3 | 3 | 4 | 5 | n | n | n | 19 | 3.80 |
| E-04-C | 4 | 4 | 5 | 4 | 5 | n | n | n | 22 | 4.40 |
| E-05-C | 4 | 3 | 3 | 4 | 5 | n | n | n | 19 | 3.80 |
| E-06-C | 2 | 2 | 1 | 2 | 1 | n | n | n | 8 | 1.60 |

-continued

Date: Month 1 of 4
Dosage: 2000 grams/day
Duration: 4 months
Equine
Study Group C
(1.82 mg/lb/day)

| Number | Mobility | Alertness | Change Positions | Pain Level | Increase Activity | Sick | Non-Use | RX Changes | Total | Average |
|---|---|---|---|---|---|---|---|---|---|---|
| E-07-C | 1 | 1 | 1 | 1 | 1 | n | n | n | 5 | 1.00 |
| E-08-C | 1 | 3 | 2 | 1 | 2 | n | n | n | 9 | 1.80 |
| E-024-C | 3 | 2 | 3 | 4 | 3 | n | n | n | 15 | 3.00 |
| E-025-C | 3 | 3 | 3 | 3 | 3 | n | n | n | 15 | 3.00 |
| Category Average | 2.75 | 2.63 | 2.63 | 2.88 | 3.13 | | | | | 2.80 |
| Average of all categories | | | 2.80 | | | | | | | |

Legend: Horse Number
E-01-C
E = Equine
01 = Horse Study Number
C = Horse Study Group Date: Month 1 of 4
Dosage: 4000 grams/day
Duration: 4 months
Equine
Study Group D
(3.64 mg/lb/day)

| Number | Mobility | Alertness | Change Positions | Pain Level | Increase Activity | Sick | Non-Use | RX Changes | Total | Average |
|---|---|---|---|---|---|---|---|---|---|---|
| E-017-D | 1 | 3 | 1 | 1 | 2 | n | n | n | 8 | 1.60 |
| E-018-D | 1 | 1 | 1 | 1 | 1 | n | n | n | 5 | 1.00 |
| E-019-D | 3 | 4 | 3 | 2 | 1 | n | n | n | 13 | 2.60 |
| E-020-D | 1 | 1 | 1 | 1 | 1 | n | n | n | 5 | 1.00 |
| E-021-D | 2 | 3 | 2 | 2 | 2 | n | n | n | 11 | 2.20 |
| E-022-D | 2 | 2 | 2 | 2 | 3 | n | n | n | 11 | 2.20 |
| E-023-D | 3 | 1 | 2 | 3 | 1 | n | n | n | 10 | 2.00 |
| Category Average | 1.86 | 2.14 | 1.71 | 1.71 | 1.57 | | | | | 1.80 |
| Average of all categories | | | 1.80 | | | | | | | |

Legend: Horse Number
E-017-D
E = Equine
017 = Horse Study Number
D = Horse Study Group Date: Month 1 of 4
Dosage: 6000 grams/day
Duration: 4 months
Equine
Study Group E
(5.46 mg/lb/day)

| Number | Mobility | Alertness | Change Positions | Pain Level | Increase Activity | Sick | Non-Use | RX Changes | Total | Average |
|---|---|---|---|---|---|---|---|---|---|---|
| E-03-E | 4 | 4 | 3 | 2 | 4 | n | n | n | 17 | 3.40 |
| E-010-E | 5 | 4 | 3 | 5 | 5 | n | n | n | 22 | 4.40 |
| E-011-E | 1 | 1 | 1 | 1 | 1 | n | n | n | 5 | 1.00 |
| E-012-E | 2 | 2 | 2 | 2 | 2 | n | n | n | 10 | 2.00 |
| E-013-E | 3 | 1 | 1 | 3 | 1 | n | n | n | 9 | 1.80 |
| E-014-E | 1 | 1 | 1 | 1 | 1 | n | n | n | 5 | 1.00 |
| E-015-E | 3 | 3 | 2 | 2 | 3 | n | n | n | 13 | 2.60 |
| E-016-E | 3 | 4 | 4 | 3 | 3 | n | n | n | 17 | 3.40 |

-continued

Date: Month 1 of 4
Dosage: 6000 grams/day
Duration: 4 months
Equine
Study Group E
(5.46 mg/lb/day)

| Number | Mobility | Alertness | Change Positions | Pain Level | Increase Activity | Sick | Non-Use | RX Changes | Total | Average |
|---|---|---|---|---|---|---|---|---|---|---|
| Category Average | 2.75 | 2.50 | 2.13 | 2.38 | 2.50 | | | | | 2.45 |
| Average of all categories | | | 2.45 | | | | | | | |

Legend: Horse Number
E-003-E
E = Equine
03 = Horse Study Number
E = Horse Study Group It should be appreciated that the compositions of this invention may contain phycocyanin within the scope of the formulas described above, or prodrugs or analogues of these compounds or a racemic mixture of either the D or the L form. Also, minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method of treating inflammation and pain in non-human animals comprising:
    administering to a non-human animal a composition comprising phycocyanin wherein the dosage of phycocyanin consists of between about 0.23–6.80 mg/kg/day.

2. The method of claim 1 whereby the phycocyanin is administered in a dose of between about 0.32–5.08 mg/kg/day.

3. The method of claim 1 wherein the phycocyanin is administered once a day.

4. The method of claim 1 wherein the phycocyanin is administered in divided doses.

5. The method of claim 1 wherein the phycocyanin is administered to a companion animal.

6. The method of claim 5 wherein the companion animal is selected from the group consisting of a dog, a cat, and a horse.

7. The method of claim 1 wherein the phycocyanin is administered to an animal having an inflammatory disorder selected from the group consisting of osteoarthritis, rheumatoid arthritis, hip dysplasia, osteochondritis, spondylitis, spondylosis, and postoperative inflammation.

8. The method of claim 7 wherein the phycocyanin is administered to an animal having arthritis.

9. The method of claim 1 wherein the composition further includes a pharmaceutically acceptable carrier.

10. The method of claim 1 wherein the composition further includes a palatability enhancer.

11. The method of claim 1 wherein the composition is administered by a method selected from the group consisting of orally, subcutaneously, intravenously, intranasally, rectally, sublingually, and buccally.

12. A method to treating inflammation and pain in non-human companion animals comprising: orally administering to a non-human companion a composition comprising phycocyanin wherein the dosage or phycocyanin consists of between about 0.23–6.80 mg/kg/day.

* * * * *